United States Patent
D'Ambrosio et al.

(10) Patent No.: US 7,525,095 B2
(45) Date of Patent: Apr. 28, 2009

(54) METHOD AND APPARATUS FOR HUMAN BRAIN IMAGING USING A NUCLEAR MEDICINE CAMERA

(75) Inventors: Raymond C. D'Ambrosio, Fremont, CA (US); Jody L. Garrard, Elk Grove, CA (US); Moataz Karmalawy, San Ramon, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 311 days.

(21) Appl. No.: 11/383,837

(22) Filed: May 17, 2006

(65) Prior Publication Data

US 2006/0261277 A1 Nov. 23, 2006

Related U.S. Application Data

(60) Provisional application No. 60/594,935, filed on May 20, 2005.

(51) Int. Cl.
*G01T 1/166* (2006.01)
(52) U.S. Cl. .................................. 250/363.05
(58) Field of Classification Search ............. 250/363.05
See application file for complete search history.

(56) References Cited

U.S. PATENT DOCUMENTS

| | | | | | |
|---|---|---|---|---|---|
| 4,582,994 A | * | 4/1986 | Berg | ............... | 250/363.1 |
| 4,652,758 A | * | 3/1987 | Barfod | ............... | 250/363.04 |
| 6,137,109 A | * | 10/2000 | Hayes | ............... | 250/363.05 |
| 6,147,353 A | * | 11/2000 | Gagnon et al. | ............... | 250/363.05 |
| 6,150,662 A | | 11/2000 | Hug et al. | ............... | 250/363.05 |
| 6,194,725 B1 | | 2/2001 | Colsher et al. | ............... | 250/363.05 |
| 6,281,505 B1 | | 8/2001 | Hines et al. | ............... | 250/363.08 |
| 6,617,582 B2 | | 9/2003 | Stark | ............... | 250/363.05 |
| 2004/0057557 A1 | | 3/2004 | Nafstadius | ............... | 378/209 |
| 2004/0262525 A1 | | 12/2004 | Yunker et al. | ............... | 250/363.08 |

OTHER PUBLICATIONS

Philips "SKYLight Technical Specifications"; http://www.medical.philips.com/us/products/nuclearmedicine/products/skylight/tech_specs/ Apr. 14, 2005 © 2004-2005 Koninklijke Philips Electronics, N.V.

* cited by examiner

*Primary Examiner*—David P Porta
*Assistant Examiner*—Shun Lee

(57) ABSTRACT

In an imaging method, mark positions are defined for one or more detector heads (10, 12) at one or more marked angular orientations ($\theta_A$, $\theta_B$). The mark positions for at least one marked angular orientation ($\theta_B$) include a tangential offset of at least one detector head. Imaging data are acquired using the one or more detector heads following a conformal trajectory passing through the defined mark positions. The acquired imaging data are reconstructed into a reconstructed image.

20 Claims, 3 Drawing Sheets

METHOD AND APPARATUS FOR HUMAN BRAIN IMAGING USING A NUCLEAR MEDICINE CAMERA

CROSS REFERENCE TO RELATED APPLICATIONS

This application claims the benefit of U.S. provisional application Ser. No. 60/594,935 filed May 20, 2005, which is incorporated herein by reference.

BACKGROUND

The following relates to the nuclear medical imaging arts. It particularly relates to head, neck, and brain scans performed using single-photon emission computed tomography (SPECT) cameras, and will be described with particular reference thereto. However, the following relates more generally to imaging of constricted anatomical regions such as the head, neck, or limbs using movable detector heads that follow trajectories closely conforming with the outer dimensions of the imaged anatomy.

In nuclear medical imaging techniques such as SPECT, a radiopharmaceutical is administered to the patient or other imaging subject. The radiopharmaceutical is typically designed to preferentially collect in an organ or tissue type of interest. For example, an intravenously administered radiopharmaceutical that remains in the blood system can be used to image patient vasculature, or the radiopharmaceutical can be designed to collect in preselected brain tissue to measure its metabolic activity, or so forth. For nuclear medical imaging, the radioactivity of the radiopharmaceutical is limited by permissible levels of patient radiation exposure. Accordingly, the level of radioactivity is typically low, and so the gamma detectors are of high sensitivity.

To improve detector sensitivity, the detector heads are typically positioned close to the anatomical region of interest. In tomographic imaging using detector heads that revolve around the imaging subject, the detector heads preferably orbit around the patient along a conformal path or trajectory that varies as a function of angular position to keep the detector heads close to the organ or region of interest without directly contacting the subject during the scan.

Many nuclear cameras are built with large gamma detector heads suitable for torso and body scans. Each gamma detector head typically includes: a honeycomb or other type of radiation collimator made of lead or another material with high radiation stopping power; scintillators that convert radiation to bursts of light; and photomultiplier tubes (PMTs), photodiodes, or other optical detectors for detecting the scintillation bursts. In some gamma cameras, each detector head has a radiation-sensitive area of about 40 cm×50 cm.

The combination of a close conformal path and relatively large-area detector heads can make tomographic SPECT imaging of constricted anatomical regions such as the head, neck, or limbs problematic. In the case of tomographic head or neck imaging, for example, the patient's shoulders can interfere with the detector head or with a mounting stricture supporting the detector head.

To improve conformity of the detector orbits with the external shape of the patient, it is known to use the detectors in an "asymmetrical" manner, in which an area of the detector face other than the geometrical center is aligned with the organ or region of interest. By aligning an edge region of the detector (e.g., 20 cm×20 cm) with the patient's head, for example, a closer positioning of the radiation detector head may be possible. In some approaches, data is collected using the entire detector face, and only data from the portion of the detector face yielding high counts is retained. However, this approach has been found to compromise image resolution. An improved approach defines a restricted "zoom" area of the gamma detector, and only the zoom area (e.g., 20 cm×20 cm) is used for collecting data.

These techniques are not wholly satisfactory for tomographic imaging of constricted anatomical regions. The off-center zoom area of the detector will often be optimal only for a limited portion of the conformal trajectory. In other trajectory portions, the choice of zoom may not be beneficial, and indeed may even be detrimental. Moreover, in the usual case where the SPECT camera includes two or more gamma detector heads, the zoom area of opposing detector heads should generally have aligned zoom areas. This imposes further compromises upon selection of the zoom area, since an optimal zoom area for one detector may be non-optimal for the opposing detector.

The following contemplates improved apparatuses and methods that overcome the aforementioned limitations and others.

BRIEF SUMMARY

According to one aspect, an imaging method is provided. Mark positions are defined for one or more detector heads at one or more marked angular orientations. The mark positions for at least one marked angular orientation include a tangential offset of at least one detector head. Imaging data are acquired using at least the one or more detector heads following a conformal trajectory passing through the defined mark positions. The acquired imaging data are reconstructed into a reconstructed image.

According to another aspect, a processor is configured to perform the imaging method set forth in the first paragraph of this Summary in conjunction with a gamma camera that includes the one or more detector heads.

According to another aspect, an imaging apparatus is provided for performing the imaging method set forth in the first paragraph of this Summary.

According to another aspect, a method of imaging with a nuclear camera that includes at least one detector head is provided. The detector head has a radiation receiving face. An active subregion of the radiation receiving face is defined which is active to receive radiation and deactivating a remainder of the radiation receiving face. The active subregion is sized in accordance with a region of interest of a subject to be imaged. The detector head is moved in a path around the region of interest. The moving includes moving the detector head with circumferential, radial, and tangential components of motion. As the detector head moves, the active subregion on the radiation receiving face is dynamically shifted to maintain the active region aligned with the region of interest.

According to another aspect, an imaging system is disclosed, comprising at least one nuclear camera detector head having a radiation receiving face, and a processor. The processor defines an active subregion of the radiation receiving face which is active to receive radiation and deactivates a remainder of the radiation receiving face, the active subregion being sized in accordance with a region of interest of a subject to be imaged; controls head-moving mechanical components to move the detector head in a path around the region of interest including moving the detector head with circumferential, radial, and tangential components of motion; and, as the detector head moves, dynamically shifts the active subregion on the radiation receiving face to maintain the active region aligned with the region of interest.

One advantage resides in improved image resolution.

Another advantage resides in improved signal sensitivity.

Another advantage resides in enabling more precisely conformal tomographic trajectories for radiation detector heads.

Another advantage resides in facilitating studies of constricted anatomical regions such as the head, neck, or limbs using gamma cameras with large-area detector heads.

Numerous additional advantages and benefits will become apparent to those of ordinary skill in the art upon reading the following detailed description.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

FIGS. 2A and 2B illustrate the lateral marking position, which also corresponds to the terminal position of the first half of the illustrated example tomographic trajectory described herein.

FIGS. 3A and 3B illustrate the anterior-posterior marking position, which also corresponds to the starting position of the first half of the illustrated example tomographic trajectory described herein.

FIGS. 4A and 4B illustrate the starting position of the second half of the illustrated example tomographic trajectory described herein.

FIGS. 5A and 5B illustrate the terminal position of the second half of the illustrated example tomographic trajectory described herein.

DETAILED DESCRIPTION OF THE PREFERRED EMBODIMENTS

Figure 1:
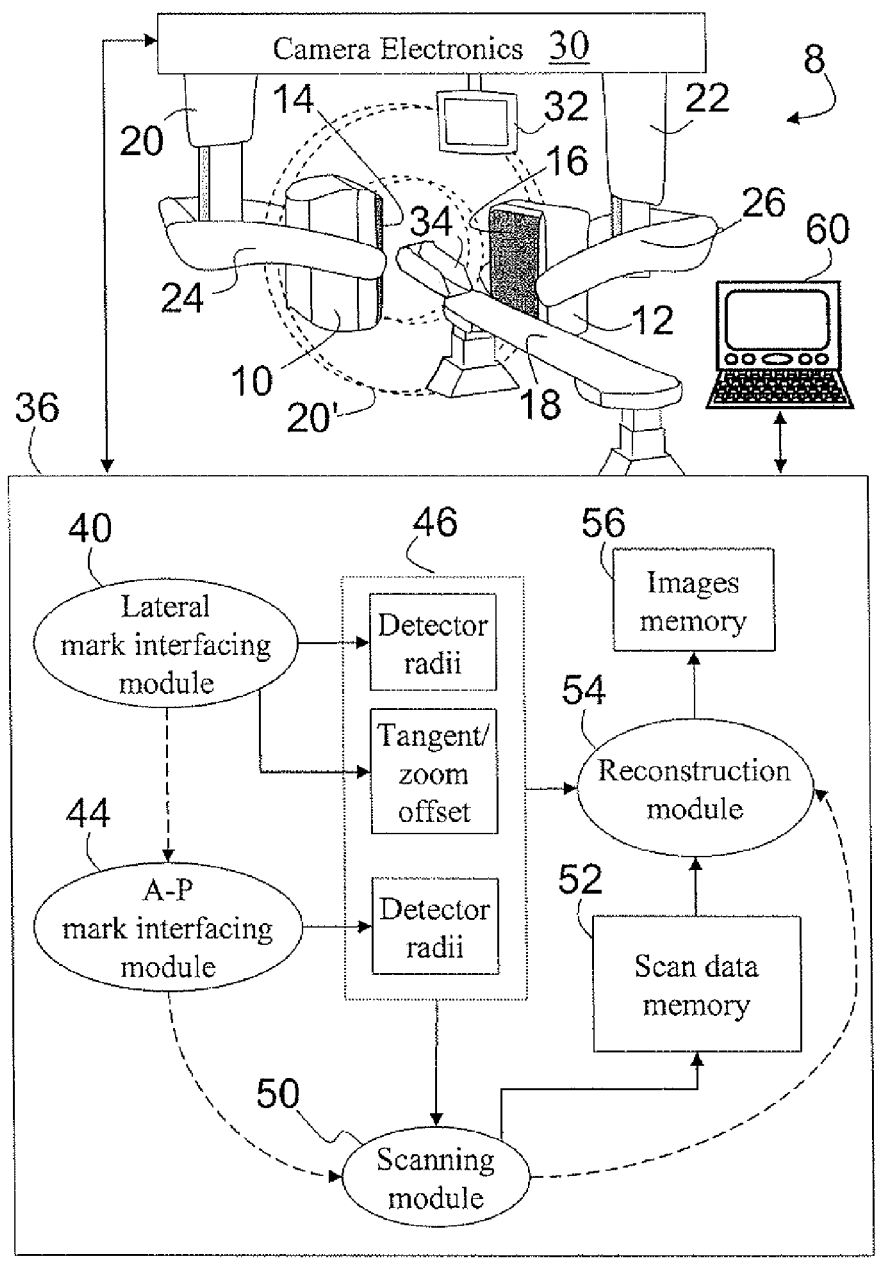
FIG. 1 diagrammatically shows a nuclear medical imaging system configured for imaging the head, neck, or other constricted anatomical region of a patient.

With reference to FIG. 1, a nuclear medical imaging system includes a gamma camera 8, which is a two-detector head camera having first radiation detector head 10 and second radiation detector head 12. The radiation detector heads 10, 12 have radiation-sensitive faces 14, 16, respectively, which in FIG. 1 are generally arranged to face a patient support or couch 18. Although not shown at the level of detail of FIG. 1, in typical embodiments the radiation-sensitive faces 14, 16 each include a honeycomb collimator (optionally detachable and replaceable to enable a selection of collimation characteristics), a scintillator arranged to receive the collimated radiation, and photomultiplier tubes (PMTs), photodiodes, or other optical detectors arranged to detect the scintillations. However, the radiation-sensitive faces 14, 16 can employ other radiation detection technologies, such as solid-state CZT-based detectors. Moreover, the number of detector heads can be one or can be greater than two.

In FIG. 1, the detector heads 10, 12 are supported by articulated, multi-jointed robotic arms 20, 22, respectively. Each robotic arm 20, 22 includes a combination of electronically controllable translational, rotational, swivel, or other mechanical joints that collectively enable radial movement of the detector heads 10, 12 toward or away from the patient couch 18, tangential movement of the heads in a direction transverse to the radial movement, and circumferential movement. Each robotic arm 20, 22 terminates in a forked support member 24, 26, respectively. The forked support members 24, 26 directly support the detector heads 10, 12, respectively.

Camera electronics 30 provide control of the articulated robotic arms 20, 22, deliver power to the robotic arms 20, 22 and the detector heads 10, 12, and output radiation detection information from the detector heads 10, 12. The camera electronics 30 are optionally coupled with a video monitor 32 for displaying various information about the status and operation of the gamma camera 8. In some embodiments, the video monitor 32 can output in a persistent "p-scope" mode which displays a map of radiation detections corresponding to the detector face of a selected one of the detectors 10, 12. To facilitate head and neck scans, a head support 34 is disposed at one end of the patient couch 18. The head support 34 in some embodiments has a cantilever orientation providing head tilt and neck elevation adjustments.

The illustrated gamma camera 8 including the radiation detectors 10, 12, patient support 18, robotic arms 20, 22, camera electronics 30, and video display 32 is suitably embodied by the Skylight™ nuclear camera (available from Philips Medical Systems, Eindhoven, Netherlands). Tile illustrated gamma camera 8 substantially conforms with the configuration of the Skylight™ nuclear camera, which has certain advantageous features such as highly articulable robotic arms and convenient overhead mounting of the robotic arms and video display. However, the imaging techniques described herein can be practiced with substantially any type of gamma camera that provides one or more radiation detectors capable of conformally moving around a patient. In some embodiments, the robotic arms 20, 22 are replaced by a ring gantry 20' (drawn in phantom in FIG. 1) that supports the detector heads 10, 12. In these embodiments, the ring gantry 20' includes a rotatable gantry portion supporting the heads 10, 12 so as to enable revolving of the heads 10, 12 around the couch 18, and gamma detector head mounting fixtures (not shown) that provide radial and tangential movement of the detector heads. In either a ring gantry or robotic arm mounting arrangement, the terminating mount structure that directly connects with the radiation detector heads can be other than the illustrated forked support members 24, 26. For example, the forked support members 24, 26 could be replaced by a single-sided mounting arm, an asymmetric arrangement of several mounting posts, or so forth. The gamma camera 8 can also include other features that are, for brevity, not illustrated in FIG. 1, such as an automated collimator exchanger which is available for the Skylight™ nuclear camera and some other gamma cameras.

With continuing reference to FIG. 1, a processor 36 is configured to perform an imaging method in conjunction with the gamma camera 8. The functionality of the processor 36 is indicated diagrammatically in FIG. 1, with sub-processes and data storage indicated, imaging process flow indicated by dashed lines, and flow of parameters and data indicated by solid lines. As an illustrated example, imaging of the head or neck region is described herein. The head and neck are examples of constricted anatomical regions with neighboring larger regions (the shoulders of the patient). In the illustrated example imaging method, the detector heads 10, 12 are positioned in opposed fashion respective to the couch 18, and acquire imaging data over the course of a conformal trajectory. The trajectory of each detector head spans 180°; however, since two opposing detector heads 10, 12 are used, in effect a full 360° scan is performed. To perform a conformal scan that keeps the radiation-sensitive faces 14, 16 of the detector heads 10, 12 close to the head or neck region of interest, the imaging method employs tangential offset of the detector heads 10, 12 when the detector heads 10, 12 are in close proximity to the shoulders.

Figure 2A:
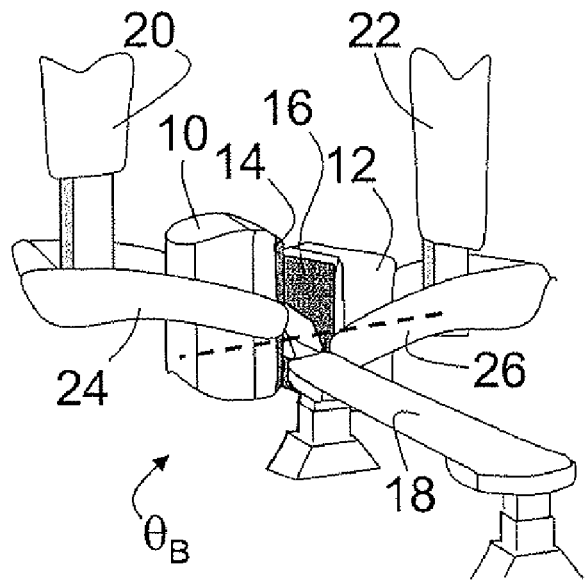
FIGS. 2A, 3A, 4A, and 5A illustrate perspective views of the two-detector head gamma camera of FIG. 1 in various positions.

With continuing reference to FIG. 1 and further reference to FIGS. 2A and 21, a lateral marking interface module 40 enables a radiologist or other user to move the heads radially and tangentially to mark selected positions for the detector heads 10, 12 near the sides of the patient that place the radiation-sensitive faces 14, 16 close to the head or neck without having the detector heads 10, 12 or the support members 24, 26 contact the shoulders. The detector heads are positioned toward the head from the shoulders, with support member 24 above the shoulder and support member 26 below the shoulder. In FIG. 21B, an imaging subject is diagrammatically indicated, lying prone on the couch 18 (not shown in FIG. 2B). A head H of the imaging subject is the region of interest, and is diagrammatically indicated. Shoulders S that limit the positioning of the detector heads 10, 12 are diagrammatically indicated using dotted lines. A plane $P_S$ of the shoulders is also indicated by a dashed line in both FIGS. 2A and 2B. The lateral marking interface allows the radiologist or other user to position the detector heads 10, 12 with tangential offsets respective to the shoulders plane $P_S$, such that the first detector head 10 is tangentially offset generally above the shoulders plane $P_S$ while the second detector head 12 is tangentially offset generally below the shoulders plane $P_S$. In this way, the forked support member 24 of the first detector head 10 is positioned above the shoulders S and does not contact the shoulders S, while similarly the forked support member 26 of the second detector head 12 is positioned below the shoulders S and does not contact the shoulders S.

Although the detector heads 10, 12 are tangentially offset generally above and below the shoulders plane $P_S$, respectively, the detector heads 10, 12 do intersect the plane of the shoulders in the marked positions that include the tangential offsets. A zoom area $Z_{1B}$ (indicated by crosshatching) on the radiation-sensitive face 14 of the first detector head 10 and a zoom area $Z_{2B}$ on the radiation-sensitive face 16 of the second detector head 12 are offset from the centers of the radiation-sensitive faces 14, 16. The offsets of the zoom areas $Z_{1B}$, $Z_{2B}$ are selected to compensate for the tangential offset of the detector heads 10, 12, respectively, such that the zoom areas $Z_{1B}$, $Z_{2B}$ are not tangentially offset from the imaging region of interest, and each zoom area $Z_{1B}$, $Z_{2B}$ remains centered on the head, neck, or other region of interest. In other contemplated embodiments, the offsets of the zoom areas only partially compensate for the tangential offsets of the detector heads, such that the brain or other region of interest is not centered in the zoom areas (but is preferably contained within the zoom areas).

In a suitable marking approach, the radiologist or other user manipulates the articulated robotic arms 20, 22 using the camera electronics 30 to position the detector heads 10, 12 in the lateral position with the detector heads 10, 12 as close as practical to the patient's head H, including tangential offsets of the detector heads 10, 12 sufficient to avoid the shoulders S. The lateral marking interface module 40 provides interfacing to allow the user to operate the robotic arms 20, 22, and causes the video display 32 to operate in a persistent (P-scope) mode to indicate the portion of each detector face 14, 16 that is detecting radiation from the brain or other region of interest in the head H. Those portions receiving radiation are defined as the zoom areas $Z_{1B}$, $Z_{2B}$. If necessary, the radiologist or other user can reposition the detector heads 10, 12 to ensure that the brain or other region of interest is completely within the zoom areas of the radiation-sensitive faces 14, 16.

Figure 3A:
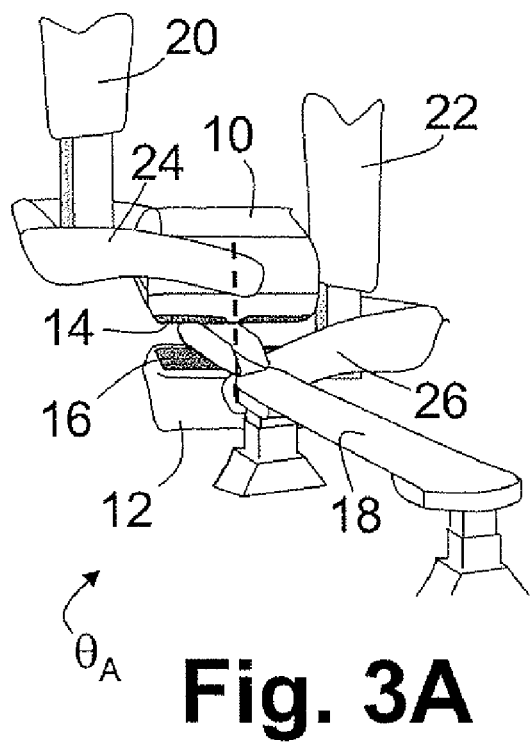
Figure 3B:
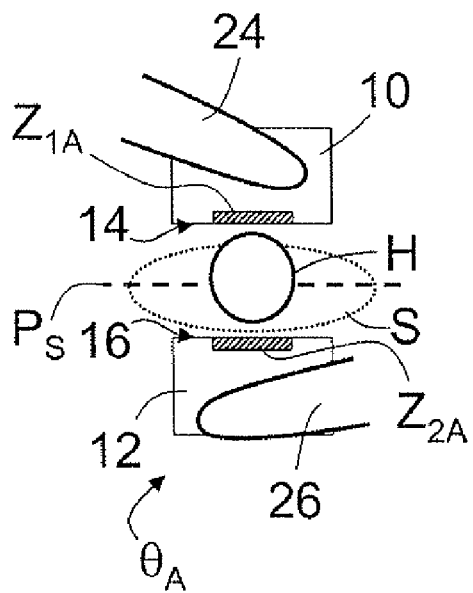

With continuing reference to FIG. 1 and with further reference to FIGS. 3A and 3B, once the mark positions for the detectors 10, 12 are determined in the lateral position, process flow transfers to an anterior-posterior mark interfacing module 44. The detector head 10 is shifted to the anterior position (above or in front of the patient) while the detector head 12 is shifted to the posterior position (behind or underneath the prone patient). The anterior-posterior mark interfacing module 44 operates similarly to the lateral mark interfacing module 42 to define mark positions for the detector head 10 in the anterior position and for the detector head 12 in the posterior position. However, because in the anterior and posterior positions the cameras are far from the shoulders S, there are no tangential offsets of the detector heads 10, 12 for the anterior and posterior positions. Zoom areas $Z_{1A}$, $Z^{2A}$ of the detector heads 10, 12, respectively, are also suitably centered on the radiation-sensitive faces 14, 16, respectively, without zoom area offsets.

With continuing reference to FIG. 1, the result of the marking is a set of conformal trajectory parameters 46, including radii of the detectors 10, 12 in the lateral and anterior-posterior angular orientations, and for the lateral angular orientation, tangent offset and zoom area offset values. The conformal trajectory parameters 46 define mark positions for the detector heads 10, 12 in the lateral and anterior-posterior angular orientations.

With continuing reference to FIG. 1, with reference to FIGS. 2A, 2B and 3A, 3B, and with further reference to FIGS. 4A, 4B and 5A, 5B, once the mark positions for the detectors 10, 12 are determined in the anterior-posterior position, process flow transfers to a scanning module 50 which performs a study or scan in which the detector heads 10, 12 are maintained in generally opposing arrangement and make a 180° angular revolution around the patient (effectively providing 360° of imaging data due to the opposing detector heads 10, 12). The detector heads 10, 12 follow a conformal trajectory that passes through the mark positions of the heads 10, 12 defined by the radiologist or other user in conjunction with the mark interfacing modules 40, 44. The scan can be performed as a continuous scan in which imaging data are collected as the detector heads 10, 12 continuously move along the conformal trajectory. Alternatively, the scan can be performed as a step-and-shoot scan in which the detector heads 10, 12 stop at discrete angular orientations along the conformal trajectory, such as stopping at 30 intervals, and acquire imaging data at each discrete stopping angular orientation.

To avoid the shoulders, the 180° scan is performed in two 90° scan portions. A first 90° scan portion runs from an angular orientation $\theta_A$ shown in FIGS. 3A and 3B and corresponding to the anterior-posterior mark positions, and terminates at an angular orientation $\theta_B$ shown in FIGS. 2A and 2B and corresponding to the lateral mark positions. As the detector heads 10, 12 near the terminal angular orientation $\theta_B$, the tangential offsets of the detector heads 10, 12 are introduced and the zoom area of each detector head is offset in the direction opposite to its tangential offset so as to compensate for the tangential offset. The tangential offsets can be introduced gradually, for example by an equal shift for each 3° rotation interval, over a smaller angular range near terminal angular orientation $\theta_B$, or abruptly at a selected angular orientation near orientation $\theta_B$.

Figure 2B:
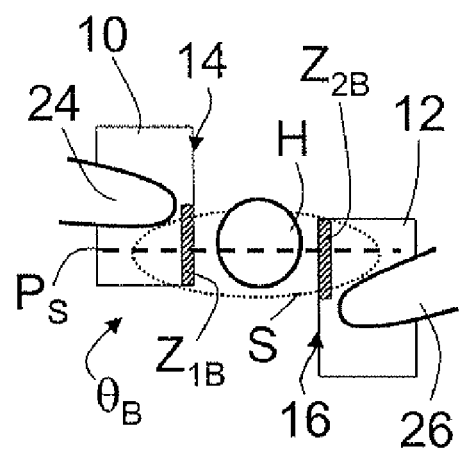
FIGS. 2B, 3B, 4B, and 5B show diagrammatic end views of the detector heads in the positions of FIGS. 2A, 3A, 4A, and 5A, respectively, with the patients shoulders and head diagrammatically indicated, and the zoom area of each detector head indicated by cross-hatching.

At the terminal angular orientation $\theta_B$, it can be seen in FIG. 2B that, notwithstanding the tangential offsets, further angular rotation would cause the forked support members 24, 26 to impinge upon the shoulders S.

Figure 4A:
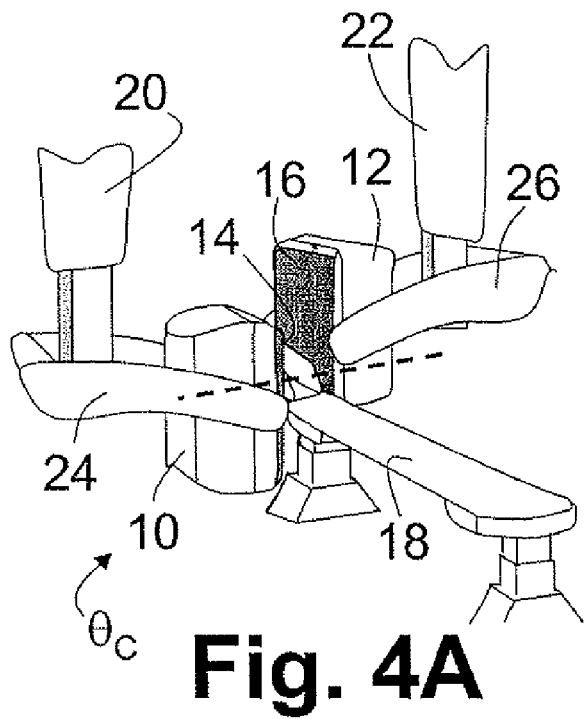
Figure 4B:
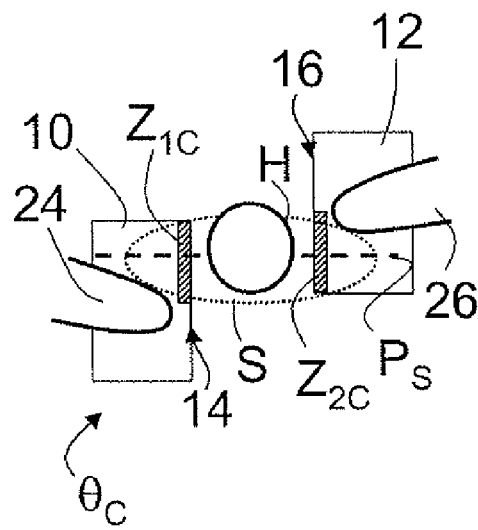

Accordingly, with further reference to FIGS. 4A and 4B, data collection is paused as the detector heads 10, 12 are drawn away from the imaging subject (that is, are moved to a relatively large radius, such as is shown in FIG. 1), are moved around the shoulders S, and moved back in toward the imaging subject to achieve the configuration of angular orientation $\theta_C$ shown in FIGS. 4A and 4B where data collection is recommenced. The angular orientation $\theta_C$ is the starting angular orientation for the second 90° portion of the 180° scan. In the illustrated embodiment which employs marking at only the angular orientations $\theta_A$ and $\theta_B$, the positions of the detector heads 10, 12 at angular orientation $\theta_C$ are suitably mirror arrangements of the mark positions of these detector heads at the angular orientation $\theta_B$. Thus, in the angular orientation $\theta_C$, the tangential offsets are arranged respective to the shoulders plane $P_S$ such that the first detector head 10 is tangentially offset generally below the shoulders plane $P_S$ while the second detector head 12 is tangentially offset generally above the shoulders plane $P_S$. In this way, the forked support member 24 of the first detector head 10 is positioned below the shoulders S and does not contact the shoulders S, while similarly the forked support member 26 of the second detector head 12 is positioned above the shoulders S and does not contact the shoulders S. The radius of the detector head 10 in the angular orientation $\theta_C$ is the same as the radius of the detector head 12 in the angular orientation $\theta_B$, while the radius of the detector head 12 in the angular orientation $\theta_C$ is the same as the radius of the detector head 10 in the angular orientation $\theta_B$.

Figure 5A:
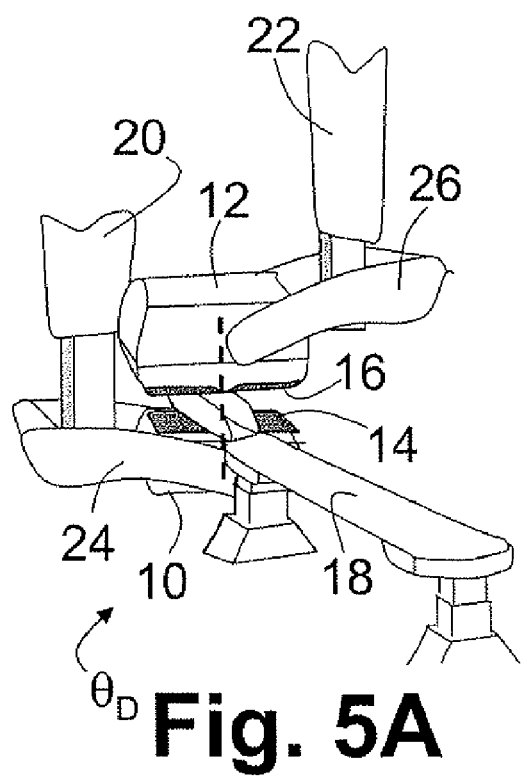
Figure 5B:
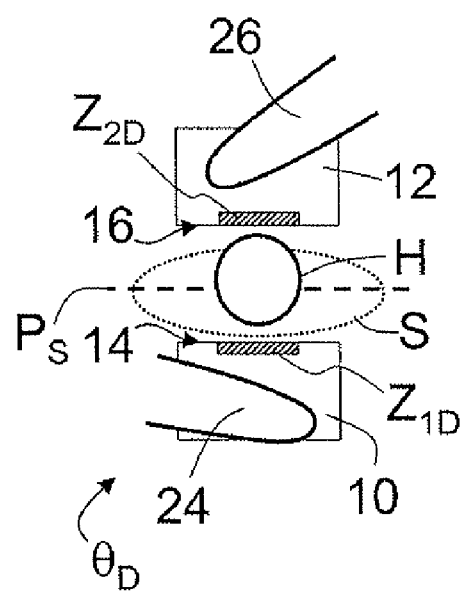

With continuing reference to FIGS. 4A, 4B and with further reference to FIGS. 5A, 5B, once the gamma camera 8 is configured in the starting angular orientation $\theta_C$, the scanning continues in the same rotational direction as before. The detector head 10 starts moving generally downward, away from the proximate shoulder, while the detector head 12 starts moving generally upward. As scanning progresses away from the lateral angular orientation $\theta_C$ shown in FIGS. 4A and 4B, the tangential offsets of the detector heads 10, 12 and the zoom areas ($Z_{1C}$, $Z_{2C}$) are offset, either gradually or abruptly, a selected angular distance away from the lateral angular orientation $\theta_C$. Scanning continues over 90°, reaching the terminal angular orientation $\theta_D$ shown in FIGS. 5A and 5B. In the angular orientation $\theta_D$, the first detector head 10 is now in the posterior position while the second detector head 12 is in the anterior position. It will be recognized that at angular orientation $\theta_D$, the mark positions and zoom areas ($Z_{1D}$, $Z_{2D}$) are a mirror arrangement of the mark positions and zoom areas ($Z_{1A}$, $Z_{2D}$) of angular orientation $\theta_A$; accordingly, where only the two angular orientations $\theta_A$, $\theta_B$ are marked, the radius of the detector head 10 in the angular orientation $\theta_D$ is the same as the radius of the detector head 12 in the angular orientation $\theta_A$, and the radius of the detector head 12 in the angular orientation $\theta_D$ is the same as the radius of the detector head 10 in the angular orientation $\theta_A$.

The illustrated example scan runs in a first portion from angular orientation $\theta_A$ to $\theta_B$, followed by resetting of the detector heads 10, 12 to the angular orientation $\theta_C$, followed by a second scan portion running from angular orientation $\theta_C$ to angular orientation $\theta_D$. Other scan portion orderings can be employed. For example, the scan can start at $\theta_B$ and run to $\theta_A$, or from at $\theta_D$ and run to $\theta_B$. The achievable ranges are dependent upon the type of mechanical support used for the detector heads. For example, a single-portion scan starting at $\theta_B$, rotating to $\theta_A$, and then continuing on until detector head 10 reached the opposite lateral angular orientation (not illustrated), is not feasible with the robotic arms 20, 22, because the arms 20, 22 would run into each other before reaching the end of the scan. On the other hand, if the ring gantry 20' is employed instead of the robotic arms 20, 22, then such a scan running from $\theta_B$ to $\theta_A$ and onward to the opposite lateral angular orientation may be feasible, depending upon the angular range of the ring gantry 20'. The acquired imaging data is suitably stored in a scan data memory 52. Still further, if the number of detector heads is different from two, or if two heads are used but are arranged other than in diametric opposition, then other scan sequences may be used. For example, a single detector head mounted on a ring gantry can make a complete 360° revolution around the imaging subject, introducing suitable tangential offsets as the single detector head approaches toward and then recedes from each shoulder so as to achieve high conformity of the trajectory with the head, neck, or other constricted anatomical region of interest.

A reconstruction module 54 employs filtered backprojection, iterative backprojection, Fourier reconstruction, or another suitable reconstruction algorithm to reconstruct the imaging data into a reconstructed image that is stored in an images memory 56. In performing the reconstruction, imaging data is translationally shifted to correct for tangential offsets of the detector heads 10, 12 during acquisition. In embodiments in which the zoom area offsets completely compensate for the tangential offsets through the entire conformal trajectory (so that the region of interest remains centered in the zoom areas throughout the scan), the translational shift is suitably equal to the offset of the zoom area. In some embodiments, the translational shift correction is performed as part of the data acquisition, so that the imaging data stored in the scan data memory 52 is already corrected. In such embodiments, the reconstruction module 54 does not perform a correction.

The reconstructed image can be displayed on a user interface 60, printed, transmitted over a hospital network or the Internet, stored electronically, magnetically, or optically, or otherwise utilized. In some embodiments, the user interface 60 includes a computer. The processor 36 configured to perform the imaging method in conjunction with the gamma camera 8 can be embodied by the same computer as the user interface 60, or can be a separate computer in communication with the user interface 60. The processor 36 can be an ASIC chip, a programmable microcontroller or microprocessor, a dedicated computer, various combinations thereof, or so forth.

In the illustrated embodiment, only the angular orientations $\theta_A$ and $\theta_B$ are marked. The detector head positions for the angular orientation $\theta_C$ are derived by symmetrical mirroring of the detector head positions and zoom areas ($Z_{1C}$, $Z_{2C}$) positions relative to the angular orientation $\theta_B$, and the detector head positions for the angular orientation $\theta_D$ are derived by symmetrical mirroring of the detector head positions and zoom areas ($Z_{1D}$, $Z_{2D}$) positions relative to the angular orientation $\theta_A$. In other embodiments, it is contemplated to mark three or all four of the angular orientations $\theta_A$, $\theta_B$, $\theta_C$, $\theta_D$. Additional angular orientations may be marked if the patient is highly asymmetric. Additionally or alternatively, the user interface 60 can enable the radiologist or other user to modify the conformal trajectory during the scan, for example to account for patient asymmetries. In other embodiments, other angular orientations may be marked. For example, if the gamma camera includes three heads spaced 120° apart, and the scan is performed over 120°, the marked positions may be spaced apart by 60°, and typically only one detector head will be proximate to a shoulder (and hence tangentially offset) at any given angular orientation.

The imaging techniques described herein can be used for other constricted anatomical regions in which detector head movement is limited by a spatially extended portion of the imaging subject. For example, imaging of the legs may be constricted by the hips. Moreover, a constricted anatomical region may be constricted by non-anatomical considerations. For example, a leg or other spatially extended portion of the couch 18 or other support structure may be readily compensated by the tangential offsets, zoom area offsets, and associated translational data corrections described herein, so as to achieve a more closely conformal detector heads trajectory.

Still further, the imaging method can be performed in conjunction with substantially any imaging modality that employs radiation detectors that follow a conformal tomographic trajectory about the imaging subject. For example, the method can be performed in conjunction with single-photon emission computed tomography (SPECT) or positron emission tomography (PET) when the scanner employs radiation detectors that revolve conformally around the patient.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiment, the invention is now claimed to be:

1. An imaging method comprising:
    defining mark positions for one or more detector heads at one or more marked angular orientations to define a zoom area on each detector head, the mark positions for at least one marked angular orientation including a tangential offset of at least one detector head;
    rotating the one or more detector heads around a subject following a conformal trajectory;
    during the rotating, tangentially shifting the zoom area on each of the one or more detector heads and acquiring imaging data using the zoom area of each of the one or more detector heads; and
    reconstructing the imaging data from the tangentially shifted zoom areas into a reconstructed image.

2. The imaging method as set forth in claim 1, wherein the reconstructing includes translationally shifting imaging data to correct for the tangential shifting of the zoom areas during the image data acquisition.

3. The imaging method as set forth in claim 1, wherein the zoom area is tangentially offset from a center of the detector head in one direction for some of the angular orientations and offset in an opposite direction in other of the angular orientations to compensate for tangential movement of the detector heads during the rotating.

4. The imaging method as set forth in claim 1, wherein the offsets of the zoom areas are tangentially shifted to keep the zoom area centered on a region of interest of the subject.

5. The imaging method as set forth in claim 1, wherein the acquiring of imaging data following the conformal trajectory employs one of (i) continuous scanning and (ii) step and shoot scanning at a plurality of discrete angular positions.

6. The imaging method as set forth in claim 1, wherein the tangential offsets accommodate one of: (i) a spatially extended portion of an imaging subject, and (ii) a spatially extended portion of a support structure that supports an imaging subject.

7. The imaging method as set forth in claim 1, wherein
    the acquiring of imaging data acquires imaging data of a head or neck region of the subject, and the tangential offsets accommodate shoulders of the subject, and
    the one or more detector heads include a pair of diametrically opposed detector heads having opposite tangential offsets when the detector heads are near the shoulders.

8. The imaging method as set forth in claim 7, wherein the conformal trajectory includes first and second trajectory portions with:
    a first detector head tangentially offset generally above a plane of the shoulders and a second detector head tangentially offset generally below the plane of the shoulders during at least some of the first trajectory portion, and
    the second detector head tangentially offset generally above the plane of the shoulders and the first detector head tangentially offset generally below the plane of the shoulders during at least some of the second trajectory portion.

9. The imaging method as set forth in claim 8, wherein the opposed detector heads intersect the plane of the shoulders in the marked positions that include the tangential offsets.

10. The imaging method as set forth in claim 1, wherein the one or more detector heads are supported by one of (i) robotic arms, and (ii) a ring gantry.

11. A processor configured to perform the imaging method of claim 1 in conjunction with a gamma camera that includes the one or more detector heads.

12. An imaging apparatus for performing the imaging method of claim 1.

13. The imaging apparatus as set forth in claim 12, including a gamma camera that includes the one or more detector heads.

14. The imaging apparatus as set forth in claim 13, further including a processor configured to perform an imaging method in conjunction with the gamma camera, the method including:
    defining mark positions for one or more detector heads at one or more marked angular orientations, the mark positions for at least one marked angular orientation including a tangential offset of at least one detector head,
    acquiring imaging data using the one or more detector heads following a conformal trajectory passing through the defined mark positions, and
    reconstructing the acquired imaging data into a reconstructed image.

15. A method of imaging with a nuclear camera that includes at least one detector head, which detector head has a radiation receiving face, the imaging method comprising:
    defining an active subregion of the radiation receiving face which is active to receive radiation and deactivating a remainder of the radiation receiving face, the active subregion being sized in accordance with a region of interest of a subject to be imaged;
    moving the detector head in a path around the region of interest including moving the detector head with circumferential, radial, and tangential components of motion;
    as the detector head moves, dynamically shifting the active subregion on the radiation receiving face to maintain the active region aligned with the region of interest.

16. The method as set forth in claim 15, further including:
    acquiring image data from the active subregion in a plurality of different shifted positions on the radiation receiving face as the detector head moves around the region of interest;

reconstructing the image data from the dynamically shifting active subregion into an image.

17. The method as set forth in claim 16, wherein the active subregion shifts tangentially as the detector head moves with the tangential components of motion to maintain the active subregion focused on the region of interest.

18. An imaging system comprising:
- at least one nuclear camera detector head having a radiation receiving face;
- a processor which:
  - defines an active subregion of the radiation receiving face which is active to receive radiation and deactivates a remainder of the radiation receiving face, the active subregion being sized in accordance with a region of interest of a subject to be imaged,
  - controls head moving mechanical components to move the detector head in a path around the region of interest including moving the detector head with circumferential, radial, and tangential components of motion, and
  - as the detector head moves, dynamically shifts the active subregion on the radiation receiving face to maintain the active subregion aligned with the region of interest.

19. The imaging system as set forth in claim 18, further including:
- a reconstruction processor which reconstructs image data acquired from the dynamically shifting active subregion as the detector head rotates around the subject to construct an image of the region of interest.

20. The imaging system as set forth in claim 19, wherein the processor further:
- controls the detector head to move at least tangentially as it rotates circumferentially around the subject to accommodate one of a spatially extended portion of the subject and a spatially extended portion of a support structure that supports the subject; and
- dynamically shifts the active subregion tangentially to offset the tangential movement of the detector head such that the active subregion remains aligned with the region of interest during the tangential movement of the detector head.

* * * * *